United States Patent
Woodland et al.

(10) Patent No.: US 10,806,690 B2
(45) Date of Patent: Oct. 20, 2020

(54) PROCESS FOR TREATING HAIR USING AQUEOUS DISPERSIONS OF PARTICULAR POLYMERS AND HEAT

(71) Applicant: L'OREAL, Paris (FR)

(72) Inventors: Frédéric Woodland, Saint-Ouen (FR); Mélissa Champeaux, Saint-Ouen (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 16/064,483

(22) PCT Filed: Dec. 19, 2016

(86) PCT No.: PCT/EP2016/081711
§ 371 (c)(1),
(2) Date: Jun. 21, 2018

(87) PCT Pub. No.: WO2017/108674
PCT Pub. Date: Jun. 29, 2017

(65) Prior Publication Data
US 2018/0369125 A1    Dec. 27, 2018

(30) Foreign Application Priority Data

Dec. 23, 2015    (FR) .................... 15 63174

(51) Int. Cl.
| A61K 8/87 | (2006.01) |
| A61K 8/895 | (2006.01) |
| A61K 8/90 | (2006.01) |
| A61K 8/04 | (2006.01) |
| A61Q 5/06 | (2006.01) |
| A61K 8/89 | (2006.01) |
| A61K 8/891 | (2006.01) |
| A61K 8/894 | (2006.01) |

(52) U.S. Cl.
CPC ................ *A61K 8/87* (2013.01); *A61K 8/04* (2013.01); *A61K 8/89* (2013.01); *A61K 8/891* (2013.01); *A61K 8/894* (2013.01); *A61K 8/895* (2013.01); *A61K 8/90* (2013.01); *A61Q 5/06* (2013.01); *A61K 2800/412* (2013.01); *A61K 2800/413* (2013.01); *A61K 2800/594* (2013.01)

(58) Field of Classification Search
CPC ... A61Q 5/06; A61K 8/87; A61K 8/89; A61K 8/891; A61K 8/894; A61K 2800/594; A61K 8/895
See application file for complete search history.

(56) References Cited

U.S. PATENT DOCUMENTS

| 3,110,695 A | 11/1963 | Ceresa | |
| 3,304,273 A | 2/1967 | Stamberger | |
| 3,383,351 A | 5/1968 | Stamberger | |
| 3,412,054 A | 11/1968 | Milligan et al. | |
| 3,523,095 A | 8/1970 | Laurito et al. | |
| 5,776,444 A * | 7/1998 | Birtwistle | A61K 8/39 424/70.11 |
| 6,800,302 B2 * | 10/2004 | Cannell | A61K 8/732 424/70.13 |
| 2005/0136025 A1 * | 6/2005 | Pataut | A61K 8/85 424/70.17 |
| 2007/0204871 A1 | 9/2007 | Singer et al. | |
| 2012/0070391 A1 * | 3/2012 | Schultze | A61K 8/898 424/59 |
| 2014/0328780 A1 * | 11/2014 | Li | A61Q 1/10 424/61 |
| 2015/0004121 A1 | 1/2015 | Tan et al. | |
| 2017/0112254 A1 * | 4/2017 | Fereyre | |

FOREIGN PATENT DOCUMENTS

| DE | 1152536 B | 8/1963 | |
| DE | 19943415 A1 | 3/2001 | |
| EP | 0874017 A2 | 10/1998 | |
| EP | 2712609 A1 | 4/2014 | |
| FR | 2782636 A1 | 3/2000 | |
| FR | 3032119 A1 | 8/2016 | |
| GB | 1040452 A | 8/1966 | |
| WO | 2010086563 A1 | 8/2010 | |
| WO | WO-2015173508 A1 * | 11/2015 | ............... A45D 1/00 |
| WO | 2016100433 A2 | 6/2016 | |
| WO | 2016100885 A1 | 6/2016 | |

OTHER PUBLICATIONS

Marchioretto et al., "Silicones Offer Multifunctional Solution for Hair Protection", Jun. 2008, retrieved from https://pdfs.semanticscholar.org/d490/ed784c07166bc1a7877c851b2c3b9e0f4ae5.pdf on Dec. 19, 2019. (Year: 2008).*

International Search Report from International Searching Authority for International Patent Application No. PCT/EP2016/081711, dated Feb. 20, 2017, 5 pages.

"Polyurethanes for Cosmetics Formulations for Hair Styling & Treatment," XP055204489, http://biotechnologia.pl/uploads/biotechnologia/product/leaflet/368854/po_czone_pliki.pdf, Retrieved Apr. 23, 2014, 26 pages.

* cited by examiner

*Primary Examiner* — Jianfeng Song
(74) *Attorney, Agent, or Firm* — The Marbury Law Group, PLLC

(57) ABSTRACT

The present invention relates to a process for treating the hair, which comprises: a) applying to hair a composition comprising at least one aqueous dispersion of silicone particles and polyurethane particles, then or simultaneously, b) heating the hair to a temperature comprised inclusively between 50° C. and 250° C. using a heating device.

11 Claims, No Drawings

PROCESS FOR TREATING HAIR USING AQUEOUS DISPERSIONS OF PARTICULAR POLYMERS AND HEAT

CROSS REFERENCE TO RELATED APPLICATIONS

This is a national stage application of PCT/EP2016/081711, filed internationally on Dec. 19, 2016, which claims priority to French Application No. 1563174, filed on Dec. 23, 2015, both of which are incorporated by reference herein in their entireties.

The invention relates to a process for treating the hair using a composition comprising at least one aqueous dispersion of silicone particles and polyurethane particles and heat.

Two major categories of hair shaping products are generally used: styling products and perming products.

Styling products allow non-permanent shaping of the hair. They are used on wet or dry hair before shaping by hand or using a brush or a comb. They may also be associated with a heating tool. They are in the form of gels, foams, waxes, pastes, lacquers or sprays. After they have been applied to the hair and after drying, these products harden substantially. This is reflected by an unnatural, embodied, dry feel required for the hold and volume of the hairstyle. Moreover, they do not show good resistance to moisture, and a head of hair loses its shape when exposed to a humid atmosphere, all the more so in a hot and humid atmosphere. Thus, firstly, the general shape of the hairstyle is rapidly lost and, secondly, the hair becomes frizzy, more particularly in the case of hair that is naturally frizzy.

To improve the feel, it is known practice to use silicones, or silicone derivatives, in particular amino silicones and amino silicones bearing silanol functions that are capable of reacting together to form new bonds. Silicones give a natural, soft, non-greasy and non-set feel. They may also be partially water-resistant, which makes it possible to conserve the soft, natural feel. However, they cannot afford shaping of the head of hair or combat the appearance of frizziness, unless a very large amount of product is applied, which gives a greasy feel on the hair and on the user's hands. As they only sparingly compensate for the dry feel when they are combined with other types of styling product such as fixing polymers, the combination of these two technologies remains relatively unsatisfactory.

Moreover, these styling products are removed on shampooing. They therefore need to be applied daily.

Perming products allow long-lasting shaping of a head of hair.

Generally, the technique used for permanently reshaping the hair consists, in a first stage, in opening the —S—S— disulfide bonds of keratin (cystine) by applying to the hair, which has been placed under tension beforehand (with curlers and other tensioning means), a reducing composition (reduction step) and then, preferably after having rinsed the head of hair thus treated, in reconstituting said disulfide bonds in a second stage by applying to the hair, which is still under tension, an oxidizing composition (oxidation step, also known as the fixing step) so as to finally give the hair the desired shape.

The new shape given to the hair by a chemical treatment such as that above is long-lasting over time and especially withstands the action of washing with water or with shampoos.

However, such a technique is not entirely satisfactory. Specifically, this technique is very effective for modifying the shape of the hair, but is very degrading to hair fibres.

These two systems do not afford sufficient cosmeticity and/or durability for the effect obtained.

Consequently, there is still a need for a hair treatment process for giving the hair a long-lasting style, in particular in the presence of moisture, while at the same time having very good cosmetic properties.

The present invention relates precisely to meeting at least one of these needs.

According to one of its features, the invention relates to a process for treating the hair that comprises:

a) applying to hair a composition comprising at least one aqueous dispersion of silicone particles and polyurethane particles, then or simultaneously, b) heating the hair to a temperature comprised inclusively between 50° C. and 250° C. using at least one heating device.

This process delivers good hairstyle hold and improves the hold durability over time, until the next wash with shampoo, especially a humid atmosphere, while preventing frizz.

In addition, it delivers hair with a cosmetic and clean feel, i.e. a non-greasy, non-sticky feel that does not transfer to the user's hands.

When it is used with a hair-shaping device, for instance an iron, the process may in particular make it possible to obtain good shaping of the hair, such as straightening/relaxing, which is long-lasting over time. It may also make it possible to durably reduce the volume of the hair and the frizziness effect.

The composition applied to hair in the process of the invention comprises an aqueous dispersion of silicone particles.

The dispersion can be a simple dispersion in the aqueous medium of the composition. Mention may be made, as a specific case of dispersions, of latexes.

The particles of silicones dispersed in water exhibit a number-average size of less than or equal to 2 microns and preferably of less than or equal to 1 micron. For example, the particles of silicones dispersed in water exhibit a number-average size ranging from 10 nm to 1 micron.

The silicone may be chosen from a linear block silicone copolymer, a polydimethylsiloxane and mixtures thereof.

The polymethylsiloxane that may be used is preferably in the form of an emulsion. According to one embodiment, the polymethylsiloxane is present in an aqueous medium in an active ingredient content of about 43% by weight, relative to the total weight of the emulsion. An example of a polymethylsiloxane emulsion is the product known under the trade name Bluesil BP 9878, sold by Bluestar Silicones; such a product uses a nonionic emulsifier.

According to a preferred embodiment, the silicone copolymer that may be used in the composition according to the invention is a linear block copolymer, i.e. a non-crosslinked copolymer, obtained by chain extension and not by cross-linking.

The term "block copolymer" (or "sequential copolymer") denotes a polymer comprising at least two distinct blocks (sequences). Each block of the polymer results from one type of monomer or from several different types of monomer. This means that each block can be composed of a homopolymer or a copolymer; this copolymer constituting the block which can in turn be random or alternating.

It should also be noted that the copolymer is "linear", in other words the structure of the polymer is neither branched, nor star-shaped, nor grafted. The linear block silicone copolymer is advantageously provided in the form of particles in dispersion in an aqueous medium.

The aqueous dispersion of block copolymer particles is a silicone-in-water (Sil/W) emulsion, the oil globules of which consist of a silicone of high viscosity, such that these globules appear to form "flexible particles".

The size of the linear block silicone copolymer particles can vary widely. Preferably, in the present patent application, the linear block silicone copolymer particles generally exhibit a number-average size of less than or equal to 2 microns and preferably of less than or equal to 1 micron.

The aqueous dispersions of linear block silicone copolymer particles used in the composition according to the invention can be chosen in particular from those described in the document EP-A-874 017, the teaching of which is incorporated herein by reference. According to this document, it is possible in particular to obtain the silicone copolymers constituting these particles by a chain-extension reaction, in the presence of a catalyst, starting from at least:

(a) a polysiloxane (i) having at least one reactive group and preferably one or two reactive groups per molecule; and (b) an organosilicone compound (ii) which reacts with the polysiloxane (i) via a chain-extension reaction.

In particular, the polysiloxane (i) is chosen from the compounds having formula (I):

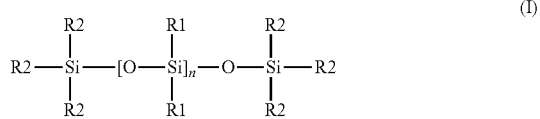

in which $R_1$ and $R_2$ represent, independently of one another, a hydrocarbon group having from 1 to 20 carbon atoms and preferably from 1 to 10 carbon atoms, such as methyl, ethyl, propyl or butyl, or an aryl group, such as phenyl, or a reactive group, and n is an integer greater than 1, provided that there are on average between one and two reactive groups per polymer.

The term "reactive group" means any group that is capable of reacting with the organosilicon compound (ii) to form a block copolymer. Mention may be made, as reactive groups, of hydrogen; aliphatically unsaturated groups, in particular vinyl, allyl or hexenyl groups; the hydroxyl group; alkoxy groups, such as methoxy, ethoxy or propoxy groups; alkoxyalkoxy groups; the acetoxy group; amino groups, and their mixtures. Preferably, more than 90% and better still more than 98% of the reactive groups are at the chain end, that is to say that the $R_2$ substituents generally constitute more than 90% and even 98% of the reactive groups.

n may especially denote an integer ranging from 5 to 30, preferably from 10 to 30 and better still from 15 to 25.

The polysiloxanes having formula (I) are linear polymers, that is to say comprising few branches and generally less than 2 mol % of siloxane units. Moreover, the $R_1$ and $R_2$ groups may optionally be substituted by amino groups, epoxy groups, groups including sulfur, silicon or oxygen.

Preferably, at least 80% of the $R_1$ groups are alkyl groups and better still methyl groups.

Preferably, the reactive $R_2$ group at the chain end is an aliphatically unsaturated group and in particular a vinyl group.

Mention may in particular be made, as polysiloxanes (i), of dimethylvinylsiloxypolydimethylsiloxane, the compound having formula (I) in which the $R_1$ substituents are methyl substituents and the $R_2$ substituents at the chain end are vinyl substituents, whereas the two other $R_2$ substituents are methyl substituents.

The organosilicone compound (ii) can be chosen from the polysiloxanes having formula (I) or the compounds which act as chain extenders. If it is a compound having formula (I), the polysiloxane (i) will comprise a first reactive group and the organosilicon compound (ii) will comprise a second reactive group which will react with the first group. If it is a chain extender, it can be a silane, a siloxane (disiloxane or trisiloxane) or a silazane. Preferably, the organosilicone compound (ii) is a liquid organohydropolysiloxane having formula (II):

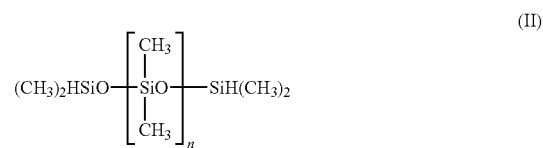

where n is an integer greater than 1 and preferably greater than 10, for example ranging from 2 to 100, preferably from 10 to 30 and better still from 15 to 25. According to a specific embodiment of the invention, n is equal to 20.

The silicone block copolymers used according to the invention are advantageously free of oxyalkylene groups, especially free of oxyethylene and/or oxypropylene groups.

The catalyst for the reaction between the polysiloxane and the organosilicon compound may be chosen from metals and especially from platinum, rhodium, tin, titanium, copper and lead. It is preferably platinum or rhodium.

The silicone copolymer particle dispersion used in the composition according to the invention may especially be obtained, for example, by mixing (a) water, (b) at least one emulsifier, (c) the polysiloxane (i), (d) the organosilicon compound (ii) and (e) a catalyst. Preferably, one of the constituents (c), (d) or (e) is added last to the mixture, in order for the chain-extension reaction to begin only in the dispersion.

Mention may be made, as emulsifiers capable of being used in the preparation process described above in order to obtain the aqueous dispersion of particles, of nonionic or ionic (anionic, cationic or amphoteric) emulsifiers. They are preferably nonionic emulsifiers which can be chosen from polyalkylene glycol ethers of a fatty alcohol comprising from 8 to 30 carbon atoms and preferably from 10 to 22 carbon atoms; polyoxyalkylenated and in particular polyoxyethylenated sorbitan alkyl esters, where the alkyl substituent comprises from 8 to 30 carbon atoms and preferably from 10 to 22 carbon atoms; polyoxyalkylenated and in particular polyoxyethylenated alkyl esters, where the alkyl substituent comprises from 8 to 30 carbon atoms and preferably from 10 to 22 carbon atoms; polyethylene glycols; polypropylene glycols; diethylene glycols; and their mixtures. The amount of emulsifier(s) is generally from 1% to 30% by weight, with respect to the total weight of the reaction mixture.

The emulsifier used in order to obtain the aqueous dispersion of particles is preferably chosen from polyethylene glycol ethers of fatty alcohols and their mixtures, and in particular polyethylene glycol ethers of alcohols comprising an alcohol of 12 or 13 carbon atoms and from 2 to 100 oxyethylene units and preferably from 3 to 50 oxyethylene units, and their mixtures. Mention may be made, for example, of $C_{12}$-$C_{13}$ Pareth-3, $C_{12}$-$C_{13}$ Pareth-23 and mixtures thereof.

According to a specific embodiment of the invention, the dispersion of silicone copolymer particles is obtained from dimethylvinylsiloxypolydimethylsiloxane (or divinyl dimethicone) as compound (i) and from the compound having formula (II) with preferably n=20 as compound (ii), preferably in the presence of a catalyst of platinum type, and the dispersion of particles is preferably obtained in the presence of $C_{12}$-$C_{13}$ Pareth-3 and $C_{12}$-$C_{13}$ Pareth-23 as emulsifiers.

Use may in particular be made, as dispersion of silicone copolymer particles, of the product sold under the name HMW 2220 by Dow Corning (CTFA name: divinyl dimethicone/dimethicone copolymer/$C_{12}$-$C_{13}$ Pareth-3/$C_{12}$-$C_{13}$ Pareth-23), which is a 60% aqueous dispersion of divinyl dimethicone/dimethicone copolymer comprising $C_{12}$-$C_{13}$ Pareth-3 and $C_{12}$-$C_{13}$ Pareth-23, said dispersion comprising approximately 60% by weight of copolymer, 2.1% by weight of $C_{12}$-$C_{13}$ Pareth-23, 2.1% by weight of $C_{12}$-$C_{13}$ Pareth-3 and 0.8% by weight of preservatives, the remainder to 100% being water.

The composition that can be used in the process of the invention may comprise an amount of silicone particles ranging from 0.5 to 15.0% by weight, preferably from 0.8 to 12.0% by weight and preferentially from 1.0 to 10.0% by weight, relative to the total weight of the composition.

The composition applied to hair in the process of the invention also comprises an aqueous dispersion of polyurethane particles.

The dispersion can be a simple dispersion in the aqueous medium of the composition. Mention may be made, as a specific case of dispersions, of latexes.

The polyurethane particles dispersed in water may have an average diameter ranging up to about 1000 nm, for example of about 50 nm to about 800 nm, or about 100 nm to about 500 nm. These particle sizes can be measured with a laser particle sizer (for example Brookhaven B190).

The polyurethane is a product of the reaction of:
A) a prepolymer having formula (III):

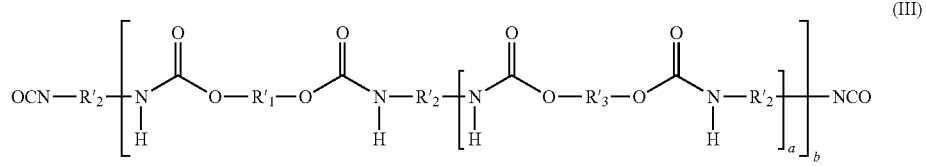

where:
R'$_1$ represents a divalent hydrocarbon substituent or a compound with dihydroxyl functionality, advantageously a substituent from a polyesterdiol,
R'$_2$ represents a hydrocarbon substituent from an aliphatic or cycloaliphatic polyisocyanate,
R'$_3$ represents a hydrocarbon substituent from a diol, optionally a low-molecular weight diol, optionally substituted by ionic groups,
a is ≤5, and
b is ≥1;
B) at least one chain lengthening agent having the formula:

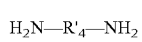

where:
R'$_4$ represents an alkylene or alkylene oxide substituent that is not substituted by ionic or potentially ionic groups; and
C) at least one chain lengthening agent having the formula:

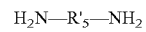

where:
R'$_5$ represents an alkylene substituent substituted by ionic or potentially ionic groups.

Prepolymer A)
Substituent R'$_1$

Appropriate compounds to provide the polyhydroxyl, preferably dihydroxyl, substituent R'$_1$ are polyesterpolyols, polyetherpolyols, polyhydroxypolycarbonates, polyhydroxy polyacetals, polyhydroxy polyacrylates, polyhydroxypolyesteramides, polyhydroxypolyalkanedienes and polyhydroxypolythioethers. Polyesterpolyols, polyetherpolyols and polyhydroxypolycarbonates are preferred. Mixtures of a number of these compounds are also part of the scope of the present invention.

Such compounds may present number average molecular weights of about 700 to about 16000, and preferably about 750 to about 5000.

The polyesterdiol(s) may generally be prepared from:
aliphatic, cycloaliphatic or aromatic dicarboxylic or polycarboxylic acids or their anhydrides and
dihydroalcohols such as diols chosen from aliphatic, alicyclic, aromatic diols.

The aliphatic dicarboxylic or polycarboxylic acids may be chosen from: succinic, fumaric, glutaric, 2,2-dimethylglutaric, adipic, itaconic, pimelic, suberic, azelaic, maleic, malonic, 2,2-dimethylmalonic, nonanedicarboxylic, decanedicarboxylic, dodecanedioic, 1,3-cyclohexanedicarboxylic, 1,4-cyclohexanedicarboxylic, 2,5-norborane dicarboxylic, diglycolic, thiodipropionic, 2,5-naphthalenedicarboxylic, 2,6-naphthalene-dicarboxylic, phthalic, terephthalic, isophthalic, oxanic, o-phthalic, tetrahydrophthalic, hexahydrophthalic or trimellitic acids.

The acid anhydrides may be in particular chosen from the anhydride of o-phthalic, trimellitic or succinic acid or a mixture thereof.

Preferably the preferred dicarboxylic acid is adipic acid.

The dihydroalcohols may be chosen from ethanediol, ethylene glycol, diethylene glycol, triethylene glycol, trimethylene glycol, tetraethylene glycol, 1,2-propanediol, dipropylene glycol, tripropylene glycol, tetrapropylene glycol, 1,3-propanediol, 1,4-butanediol, 1,3-butanediol, 2,3-butanediol, 1,5-pentanediol, 1,6-hexanediol, 2,2-dimethyl-1,3-propanediol, 1,4-dihydroxycyclohexane, 1,4-dimethylolcyclohexane, cyclohexane dimethanol, 1,8-octanediol, 1,10-decanediol, 1,12-dodecanediol, neopentyl glycol or mixtures thereof. The cycloaliphatic and/or aromatic dihydroxyl compounds are also of course suitable as dihydroalcohol(s) for the preparation of polyesterpolyol(s).

The polyester diols may also be chosen from homopolymers or copolymers of lactones, which are preferably obtained by addition reactions of lactones or mixtures of lactones, such as butyrolactone, ε-caprolactone and/or methyl-ε-caprolactone with the polyfunctional initiating molecules, preferably appropriate difunctional molecules, such as for example the dihydroalcohols cited above. The corresponding ε-caprolactone polymers are preferred.

The polyester polyol substituent $R'_1$, preferably a polyester diol, may be obtained advantageously by the polycondensation of dicarboxylic acids, such as adipic acid, with polyols, especially diols, such as hexanediol, neopentyl glycol, and mixtures thereof.

Polycarbonates containing hydroxyl groups comprise those know per se such as the products obtained by reacting diols such as 1,3-propanediol, 1,4-butanediol and/or 1,6-hexanediol, diethylene glycol, triethylene glycol or tetraethylene glycol with diaryl carbonates, for example diphenyl carbonate or phosgene.

Appropriate polyether polyols are obtained in a known manner by reacting starting compounds that contain reactive hydrogen atoms with alkylene oxides such as ethylene oxide, propylene oxide, butylene oxide, styrene oxide, tetrahydrofuran or epichlorhydrin or with mixtures of these alkylene oxides. It is preferable that the polyethers do not contain more than about 10% by weight of ethylene oxide units. In a preferred manner, the polyethers obtained are used without the addition of ethylene oxide.

Polyethers modified by vinyl polymers are also suitable for the composition that is useful in the process according to the invention. Products of this type may be obtained by the polymerization for example of styrene and acrylonitrile in the presence of polyethers (U.S. Pat. Nos. 3,383,351; 3,304,273; 3,523,095; 3,110,695 and German patent 1 152 536).

The polythioethers that ought to be mentioned in particular include the products of condensation obtained from thiodiglycol alone and/or with other glycols, dicarboxylic acids, formaldehyde, aminocarboxylic acids or aminoalcohols. The products obtained are either mixed polythioethers, polythioetheresters or polythioetheresteramides, depending on the co-components.

Appropriate polyacetals comprise the compounds that may be prepared from aldehydes, for example formaldehyde, and glycols such as diethylene glycol, triethylene glycol, ethoxylated 4,4'-dihydroxy-diphenyl-dimethylmethane and 1,6-hexanediol. Polyacetals appropriate for the needs of the invention may also be prepared by polymerizing cyclic acetals.

Appropriate polyhydroxy polyester amides and polyamines are for example the mainly linear products of condensation obtained from saturated and unsaturated polybasic carboxylic acids or their anhydrides and of saturated and unsaturated polyvalent aminoalcohols, diamines or polyamines or mixtures thereof.

Monomers appropriate for the production of polyacrylates with hydroxyl functionality comprise acrylic acid, methacrylic acid, crotonic acid, maleic anhydride, 2-hydroxyethyl acrylate, 2-hydroxyethyl methacrylate, 2-hydroxypropyl acrylate, 2-hydroxypropyl methacrylate, 3-hydroxypropyl acrylate, 3-hydroxypropyl methacrylate, glycidyl acrylate, glycidyl methacrylate, 2-isocyanatoethyl acrylate and 2-isocyanatoethyl methacrylate.

Appropriate polyalkanedienes comprise polybutadienes and polyisoprenes, such as the Poly bd resin by Elf Atochem North America, Philadelphia, Pa. Hydrogenated polyisoprene and hydrogenated polybutadiene are also comprised.

Examples of those comprise Kraton L-2203 by Shell Chemical, Houston, Tex., and the Polytail resins by Mitsubishi Chemical, Tokyo, Japan.

Mixtures of the dihydroxy compounds described above may be used.

Substituent $R'_2$

Appropriate polyisocyanates for providing the hydrocarbon substituent $R'_2$ comprise organic diisocyanates with a molecular weight of about 112 to 1000, and preferably about 140 to 400.

Preferred diisocyanates are those represented by the general formula $R'_2(NCO)_2$, in which $R'_2$ represents a divalent aliphatic hydrocarbon group comprising 4 to 18 carbon atoms, a divalent cycloaliphatic hydrocarbon group comprising 5 to 15 carbon atoms, a divalent araliphatic hydrocarbon group comprising 7 to 15 carbon atoms or a divalent aromatic hydrocarbon group comprising 6 to 15 carbon atoms. Examples of organic diisocyanates that are suitable comprise tetramethylene diisocyanate, 1,6-hexamethylene diisocyanate, dodecamethylene diisocyanate, 1,3-cyclohexane-diisocyanate and 1,4-cyclohexane-diisocyanate, 1-isocyanato-3-isocyanatomethyl-3,5,5-trimethylcyclohexane (isophorone diisocyanate or IPDI), bis(4-isocyanatocyclohexyl)-methane, 1,3-bis(isocyanatomethyl)-cyclohexane and 1,4-bis(isocyanatomethyl)-cyclohexane, bis(4-isocyanato-3-methyl-cyclohexyl)-methane. Mixtures of diisocyanates may of course be used. Preferred diisocyanates are aliphatic and cycloaliphatic diisocyanates. 1,6-Hexamethylene diisocyanate, isophorone diisocyanate and dicyclohexylmethane diisocyanate and mixtures thereof are particularly preferred.

Substituent $R'_3$

Using diols, optionally low-molecular weight diols $R'_3$ may increase rigidification in the polymer chain and is optional. The expression "low-molecular weight diols" means diols with a molecular weight of about 62 to 700, preferably from 62 to 200. They may contain aliphatic, alicyclic or aromatic groups. The preferred compounds only contain aliphatic groups. The diols used preferably have up to 20 carbon atoms and may be chosen from ethylene glycol, diethylene glycol, 1,2-propanediol, 1,3-propanediol, 1,4-butanediol, 1,3-butylene glycol, neopentyl glycol, butyl ethyl propanediol, cyclohexanediol, 1,4-cyclohexanedimethanol, 1,6-hexanediol, bisphenol A (2,2-bis(4-hydroxyphenyl)propane), hydrogenated bisphenol A (2,2-bis(4-hydroxycyclohexyl)propane), and mixtures thereof. Preferably, $R'_3$ is from neopentyl glycol.

Optionally, the low-molecular weight diols may contain ionic or potentially ionic groups. Appropriate low-molecular weight diols containing ionic or potentially ionic groups are those disclosed in U.S. Pat. No. 3,412,054. Preferred compounds comprise dimethylolbutanoic acid (DMBA), dimethylolpropionic acid (DMBA) and the caprolactone-polyesterdiol containing carboxyl. If low-molecular weight diols containing ionic or potentially ionic groups are used, they are preferably used in a quantity such that <0.30 meq of COOH is present per gram of polyurethane in the polyurethane dispersion. Preferably, low-molecular weight diols containing ionic or potentially ionic groups are not used.

The prepolymer chain is lengthened by using two classes of chain lengthening agent B) and C).

B) Chain Lengthening Agents

Compounds B) of the first chain lengthening class have the formula:

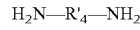

where $R'_4$ represents an alkylene or alkylene oxide substituent that is not substituted by ionic or potentially ionic groups.

Accordingly, the chain lengthener may be chosen from:

Alkylenediamines such as hydrazine, ethylenediamine, propylenediamine, 1,4-butylenediamine and piperazine.

Diamines of alkylene oxides such as dipropylamine diethylene glycol (DPA-DEG available from Tomah Products, Milton, Wis.), 2-methyl-1,5-pentanediamine (Dytec A by DuPont), hexanediamine, isophoronediamine, and 4,4-methylenedi(cyclohexylamine), and the series of DPA-etheramines available from Tomah Products, Milton, Wis., comprising dipropylamine propylene glycol, dipropylamine dipropylene glycol, dipropylamine tripropylene glycol, dipropylamine poly(propylene glycol), dipropylamine thylene glycol, dipropylamine poly(ethylene glycol), dipropylamine-1,3-propanediol, dipropylamine-2-methyl-1,3-propanediol, dipropylamine-1,4-butanediol, dipropylamine-1,3-butanediol, dipropylamine-1,6-hexanediol and dipropylamine cyclohexane-1,4-dimethanol, and mixtures thereof.

Preferably, the chain lengthener B) is chosen from ethylenediamine, diethanolamine and mixtures thereof.

C) Chain Lengthening Agents

The second class of chain lengthening agents are compounds C) with the formula:

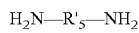

$H_2N-R'_5-NH_2$ where $R'_5$ represents an alkylene substituent substituted by ionic or potentially ionic groups. These compounds have an ionic or potentially ionic group and two groups that are reactive with isocyanate groups. The ionic or potentially ionic group may be chosen from the group constituted by tertiary or quaternary ammonium groups, groups that can be converted into such a group, a carboxyl group, a carboxylate group, a sulfonic acid group and a sulfonate group. Said at least partial conversion of groups that can be converted into salt groups of the type mentioned may take place before or during the mixing with water. Specific compounds comprise diamino sulfonates, such as for example the sodium salt of N-(2-aminoethyl)-2-aminoethanesulfonic acid (AAS) or the sodium salt of N-(2-aminoethyl)-2-aminopropionic acid.

Preferably, $R'_5$ represents an alkylene substituent substituted by sulfonic acid or sulfonate groups.

Preferably, this compound is the sodium salt of N-(2-aminoethyl)-2-aminoethanesulfonic acid (AAS).

Chain Endings

The polyurethane according to the invention may also comprise compounds that are located in each case at the chain ends and terminate said chains. These chain ends may be derived from compounds having the formula:

in which $R'_6$ represents a hydrogen atom or an alkylene substituent optionally having a hydroxyl end and $R'_7$ represents an alkylene substituent optionally having a hydroxyl end. Appropriate compounds comprise compounds such as monoamines, in particular secondary monoamines or monoalcohols. Examples comprise: methylamine, ethylamine, propylamine, butylamine, octylamine, laurylamine, stearylamine, isononyloxypropylamine, dimethylamine, diethylamine, dipropylamine, dibutylamine, N-methylaminopropylamine, diethyl(methyl)aminopropylamine, morpholine, piperidine, diethanolamine and appropriate substituted derivatives thereof, amide-amines of primary diamines and monocarboxylic acids, monoketimins of primary diamines, primary/tertiary amines such as N,N-dimethylamino-propylamine and analogues. The chain end alcohols may be chosen from $C_1$-$C_{10}$ alcohols, such as methanol, butanol, hexanol, 2-ethylhexyl alcohol, isodecyl alcohol, and mixtures thereof; aminoalcohols such as aminomethylpropanol (AMP) area also suitable.

In one embodiment of the invention, diethylene glycol is used to obtain polyurethane either as a low-molecular weight diol, or as part of the nonionic chain lengthening agent via the use of dipropylamine-diethylene glycol. In the event that diethylene glycol is used as a low-molecular weight diol, then, preferably, DPA-DEG is not used as a nonionic chain lengthening agent. In an analogous manner, if DPA-DEG is used as a nonionic chain lengthening agent, then preferably, diethylene glycol is not used as a low-molecular weight diol.

Preparation Processes for the Polyurethane Dispersion

The aqueous dispersion may be obtained via a preparation process comprising the following steps:

A) the preparation of an aqueous dispersion of polyurethane by
1) forming a prepolymer with isocyanate functionality by reacting:
   1a) a polyol, advantageously a polyester polyol, and especially a polyesterdiol,
   1b) an aliphatic or cycloaliphatic polyisocyanate, and
   1c) a low-molecular weight diol, optionally substituted by ionic groups;
2) lengthening the chain of the prepolymer by:
   2a) at least one chain lengthening agent according to the formula:

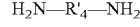

$H_2N-R'_4-NH_2$ where $R'_4$ represents an alkylene or alkylene oxide substituent that is not substituted by ionic or potentially ionic groups, and
   2b) at least one chain lengthening agent according to the formula:

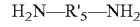

$H_2N-R'_5-NH_2$ where $R'_5$ represents an alkylene substituent substituted by ionic or potentially ionic groups,
   in the presence of an organic solvent to form a polyurethane;
3) dispersing the polyurethane in water; and
4) removing the organic solvent, which produces an aqueous polyurethane dispersion; and
mixing the polyurethane dispersion with water or ethanol.

More particularly, an appropriate production process for a polyurethane dispersion for use in the process of the invention, may comprise the following steps: a) reacting in a first step of at least one polyesterpolyol compound and a low-molecular weight diol optionally substituted by an ionic group (dihydroxyl compounds) with diisocyanate to form the prepolymer A), then b) in a second step dissolving the prepolymer in an organic solvent and c) in a third step reacting the prepolymer solution containing the isocyanate with both classes of chain lengthening agents and, optionally, the chain ending, d) in a fourth step, forming the dispersion by adding water, and e) in a fifth step, removing the organic solvent.

The free sulfonic acid groups incorporated are neutralized between the third and fourth steps. Appropriate neutralization agents are primary, secondary or tertiary amines. Among these, tertiary amines substituted by trialkyl are preferred. Examples of these amines are trimethylamine, triethylamine, triisopropylamine, tributylamine, N,N-dimethylcyclohexylamine, N,N-dimethylstearylamine, N,N-dimethylaniline, N-methylmorpholine, N-ethylmorpholine, N-methylpiperazine, N-methylpyrrolidine, N-methylpiperidine, N,N-dimethylethanolamine, N,N-diethylethanolamine, N-methyldiethanolamine, dimethylaminopropanol, 2-methoxyethyldimethylamine, N-hydroxyethylpiperazine, 2-(2-dimethylaminoethoxy)-ethanol and 5-diethylamino-2-pentanone. Preferred tertiary amines are those that do not contain any active hydrogen as determined by the Zerewitinoff test, given than hydrogen can react with isocyanate groups in the prepolymers, which can cause gelling, the formation of insoluble particles or chain ends.

The polyurethane dispersions can be produced by what we call the the acetone process. In the acetone process, the synthesis of aqueous polyurethane preparations based on the dispersions according to the invention is achieved in a process with multiple steps.

In a first step, a prepolymer containing isocyanate groups is synthesized from the polyesterpolyol compound, diisocyanate and the low-molecular weight diol. The quantities of individual components are calculated so that the isocyanate content in the prepolymers is between 1.4 and 5.0% by weight, preferably between 2.0 and 4.5% by weight, and in a particularly preferred manner between 2.6 and 4.0% by weight. The low-molecular weight diol is present in a quantity from 0 to 80% in equiv based on the quantity of NCO equivalents, preferably from 0 to 10% in equiv.

The prepolymer obtained has the structure:

form the high molecular weight polyurethane. Sufficient quantities of chain lengthening agents and chain endings are used so that the average molecular weight by number (Mn) calculated for the polyurethane obtained is between 10000 and 100000 Daltons, preferably between 10000 and 50000 Daltons. The nonionic chain lengthening agent is present in a quantity of 15 to 90% in equiv, preferably from 35.0 to 55% in equiv, based on the residual quantity of NCO equivalents present in the prepolymer. The ionic chain lengthening agent is present in a quantity of 10 to 50% in equiv, preferably from 25 to 35% in equiv, based on the residual quantity of NCO equivalents present in the prepolymer. The chain ending is present in a quantity of 0 to 35% in equiv, preferably from 20 to 30% in equiv, based on the residual quantity of NCO equivalents present in the prepolymer.

In a fourth step, the high-molecular weight polyurethane is dispersed in the form of a dispersion of fine particles by adding water to the solution or the solution to water.

In a fifth step, the organic solvent is partially or totally removed by distillation, optionally under reduced pressure. The quantity of water in the fourth step is calculated such that the aqueous polyurethane dispersions according to the invention display a solid content of 20 to 60% by weight, preferably from 28 to 42% by weight.

In at least some examples of embodiments, the polyurethane particles may have an average diameter ranging up to about 1000 nm, for example of about 50 nm to about 800 nm, or about 100 nm to about 500 nm. These particle sizes can be measured with a laser particle sizer (for example Brookhaven BI90).

According to a preferred embodiment, the aqueous dispersion of polyurethane particles may be chosen from compounds having INCI name polyurethane-34.

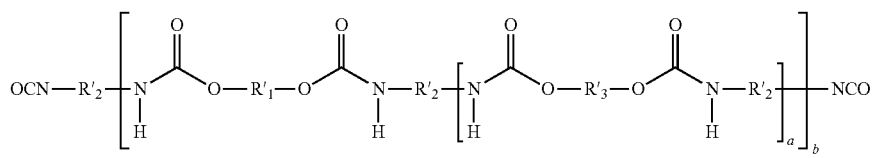

(III)

where:
R'$_1$ represents a divalent substituent or a compound with dihydroxyl functionality, advantageously a polyesterdiol,
R'$_2$ represents a hydrocarbon substituent or an aliphatic or cycloaliphatic polyisocyanate,
R'$_3$ represents a low-molecular weight diol, optionally substituted by ionic groups,
a is ≤5, and
b is ≥1.

Preferably, a ranges from 1 to 3 and b ranges from 1 to 5.

In a second step, the prepolymer produced in step 1 is dissolved in an organic solvent, that is at least partially miscible with water and contains no groups that react with isocyanate. The preferred solvent is acetone. Other solvents such as for example 2-butanone, tetrahydrofuran or dioxane or mixtures of these solvents may however also be used. The quantities of solvent to use must be calculated so that a solid content of 25 to 60% by weight, preferably from 30 to 50% by weight, in a particularly preferred manner from 35 to 45% by weight, is obtained.

In a third step, the prepolymer solution containing isocyanate is reacted with mixtures of chain lengthening agents with amino functionality and, optionally, chain endings, to As non-limiting examples of aqueous polyurethane dispersions, mention may be made of those sold under the name Baycusan® by Bayer such as, for example, Baycusan® C1000 (INCI name: polyurethane-34), Baycusan® C1001 (INCI name: polyurethane-34), Baycusan® C1003 (INCI name: polyurethane-32), Baycusan® C1004 (INCI name: polyurethane-35) and Baycusan® C1008 (INCI name: polyurethane-48). In various exemplary embodiments, polyurethane latexes may be chosen from, but are not limited to, aqueous polyurethane dispersion of Isophthalic Acid/Adipic Acid/Hexylene Glycol/Neopentyl glycol/Dimethylolpropanoic Acid/Isophorone Diisocyanate copolymer (INCI name: Polyurethane-1, such as Luviset® P.U.R, BASF), aliphatic polyurethane and aliphatic polyester polyurethane (such as the Neorez® series, DSM, such as Neorez® R989, INCI name: Polycarbamyl Polyglycon Ester).

The composition that can be used in the process of the invention may comprise an amount of polyurethane particles ranging from 0.2 to 10.0% by weight, preferably from 0.3 to 8.0% by weight and preferentially from 0.5 to 5.0% by weight, relative to the total weight of the composition.

Preferably, the silicone and polyurethane particles are present in an silicone/polyurethane weight ratio ranging from 0.1 to 10, more preferentially from 0.5 to 10 and better still from 1 to 8.

Before being added to the composition used in the process according to the invention, the aqueous dispersions of silicone and polyurethane may be dispersed in independent dispersion media, or, as a variant, be dispersed in the same dispersion medium.

The dispersion medium or media comprise water. The dispersion medium or media comprising water may also comprise one or more organic solvents that are liquid at 25° C., $1.013 \times 10^5$ Pa, especially water soluble organic solvents, such as $C_1$-$C_7$ alcohols, and especially aliphatic or aromatic $C_1$-$C_7$ monoalcohols, $C_3$-$C_7$ polyols and polyol ethers, hydrocarbons, such as, for example, isododecane and mineral oil; and silicones, such as dimethicones, cyclomethicones, and cyclopentasiloxane; and mixtures thereof.

Preferably, the silicone particles and polyurethane particles are not soluble in the solvent of the dispersion medium, i.e. are not soluble in water and/or in at least one organic solvent. Consequently, the polyurethane and the silicone retain their specific shape in the solvent(s).

Preferably, the composition according to the invention is aqueous and comprises water at a concentration preferably ranging from 5% to 99% by weight, in particular from 20% to 98% by weight and better still from 50% to 98% by weight, relative to the total weight of the composition.

The composition may also comprise, independently of the dispersion medium, one or more organic solvents that are liquid at 25° C., $1.013 \times 10^5$ Pa, especially water soluble organic solvents, such as $C_1$-$C_7$ alcohols, and especially aliphatic or aromatic $C_1$-$C_7$ monoalcohols, $C_3$-$C_7$ polyols and polyol ethers, hydrocarbons, such as, for example, isododecane and mineral oil; and silicones, such as dimethicones, cyclomethicones, and cyclopentasiloxane; and mixtures thereof.

The organic solvents, when they are present, generally represent from 0.01 to 40% by weight and preferably from 5 to 35% by weight relative to the total weight of the composition.

The composition that may be used in the process according to the invention may also comprise one or more additives chosen from surfactants, preferably chosen from nonionic, anionic, cationic and amphoteric surfactants, fixing polymers, conditioning agents preferably chosen from cationic polymers, silicones, thickening agents, hydrophilic solvents, hydrophobic solvents, UV filters, fillers such as nacres, titanium dioxide, resins and clays, fragrances, peptizers, vitamins, preservatives, acidic agents, alkaline agents, reducing agents, oxidizing agents, direct dyes, in particular those chosen from cationic and natural direct dyes, oxidation dyes, and a mixture of these compounds.

A person skilled in the art will take care to select the optional additives and the amounts thereof so that they do not interfere with the properties of the compositions of the present invention.

These additives may each be present in the composition according to the invention in a content ranging from 0 to 20% by weight, relative to the total weight of the composition.

The composition may be in the form of a foam, a gel, a serum, a cream, a paste, a wax, a liquid lotion or a lacquer. Preferably, the composition is in the form of a serum or a liquid lotion.

The composition may be packaged in a pump-dispenser bottle or in an aerosol device. As a variant, it may be envisaged to package it in a container intended to be received in a refillable application device. The container is then in the form of a refill, especially intended for a single product application. In other words, the device may be used with a new product refill during subsequent application.

In the process according to the invention, the composition that has just been described is applied to wet or dry hair, preferably to wet hair.

The process according to the invention may also comprise a step b) of heating the hair at a temperature between, limits inclusive, 50° C. and 250° C., preferably 90° C. and 250° C., more preferably 120° C. and 230° C., and even better still between 150° C. and 230° C.

The step b) of heating the hair may be performed with any type of device known in the art for obtaining a temperature on the hair of at least 50° C.

The heating step b) may especially be performed using a heating device chosen from a straightening iron, a curling iron, a crimping iron, a waving iron, a hair drying hood or a hairdryer, preferably using a straightening iron.

According to a preferred embodiment, the heating step may comprise a step of drying the hair using a hairdyer, using or not using a brush to style the hair, then a step of heating the hair using an iron chosen from a straightening iron, a curling iron, a crimping iron, a waving iron, preferably using a straightening iron.

According to the invention, the process also comprises a step c) of applying steam to the hair by means of a device that is capable of generating steam.

The heating step c) may precede, follow or be simultaneous with the steam application step b).

Preferably, the heating step b) may follow the steam application step c).

Steam may be applied using any device known per se for generating the amount of steam of use in the process of the invention. According to a particular embodiment, this device is portable, that is to say that the tank which makes it possible to generate the steam is in contact with the part of the device comprising the orifices for dispensing the steam.

The steam may be dry. The term "dry steam" means a gas which contains only water molecules in gaseous form.

The steam may alternatively be wet. The term "wet steam" means a gas which contains water molecules in gaseous form and water molecules in liquid form.

Preferably, the process according to the invention comprises a step of applying steam after step a).

The amount of steam may be, limits inclusive, between 0.5 and 60 g/min, preferably between 1 and 20 g/min, more preferably 2 and 10 g/min and better still 2 and 5 g/min.

Preferably, the application time of steam on the hair, per tress, ranges from 1 second to 50 minutes, preferably from 1 second to 10 minutes and more preferably from 1 second to 1 minute. For example, the application time of steam on the hair may be from about 10 to 15 seconds.

According to a particular embodiment, the steam applied to the hair contains one or more cosmetic active agents and/or ingredients such as a fragrance, a shaping or conditioning active agent, etc.

According to a particular embodiment, the application of steam and the heating of the hair are performed by a single device, preferably a device chosen from a steam-generating straightening iron, a steam-generating curling iron, a steam-generating crimping iron and a steam-generating waving iron, more preferably by a steam-generating straightening iron.

According to a preferred embodiment, the application of steam and the heating of the hair are performed by a single device in which the application of steam and the heating are dissociated.

In other words, for a treated hair tress, the steam application step and the heating step are not performed simultaneously on the same portion of hair, though it is nevertheless possible for these two steps to be performed with the same machine configured to form these two steps successively. According to this embodiment, the steam is distributed by the device from the exterior of the heating elements. Alternatively, two separate machines can be used to carry out these unconnected stages.

The application of heat and/or steam may be repeated several times on the same fibres, or may only be repeated once, or preferably may only be repeated twice.

According to a preferred embodiment of the invention, the hair treatment process comprises:

a) a step of applying a composition as described previously, followed by
b) a step of drying hair with a hairdryer, with or without styling, especially using a brush, followed by
c) a step of heating hair using a heating device chosen from a straightening iron, a curling iron, a crimping iron and a waving iron, preferably using a straightening iron, even more preferably a steam-generating straightening iron, where the steam can be applied before the heating step with the iron.

The invention is illustrated in greater detail in the examples that follow, which are given as non-limiting illustrations of the invention.

EXAMPLES

The following compositions were prepared, the contents being expressed by weight with respect to the total weight of the composition:

| Ingredients (INCI name and trade names) | A | B (comparative) |
|---|---|---|
| DIVINYLDIMETHICONE/DIMETHICONE COPOLYMER (60% AI) (and) C12-13 PARETH-3 (and) C12-13 PARETH-23 (HMW 2220 NON-IONIC EMULSION by DOW CORNING) | 2.5 | — |
| POLYURETHANE-34 (32% AI) (BAYCUSAN C 1001 by BAYER MATERIALSCIENCE) | 4.69 | 3.13 |
| ACRYLATES COPOLYMER (27% AI) (LUVIFLEX SOFT by BASF) | — | 3.7 |
| ETHYLHEXYLGLYCERIN | 0.1 | 0.1 |
| Preservative | 0.9 | 0.9 |
| Water | qs 100 | qs 100 |

Control process: A natural, dry, curly hair tress was then treated twice with a smoothing iron heated to 210° C. applying dry steam with a flow rate of 3.3 g/min. The passage time for the straightening tongs was 15 s.

On the same types of dry hair, compositions A and B were applied, with a bath ratio of 0.5 g/g.

Invention process 1: After applying composition A, the tresses were styled with a round brush and a hairdryer, the temperature at the hairdryer's outlet being 80° C. The step of heating with a hairdryer was followed by two passes on each tress with smoothing iron at 210° C. applying dry steam with a flow rate of 3.3 g/min. For each tress, the time for passage of the smoothing iron was 15 s.

Comparative process: After applying composition B, the tresses were styled with a round brush and a hairdryer, the temperature at the hairdryer's outlet being 80° C. The step of heating with a hairdryer was followed by two passes on each tress with smoothing iron at 210° C. applying dry steam with a flow rate of 3.3 g/min. For each tress, the time for passage of the smoothing iron was 15 s.

Invention process 2: After applying composition A, the tresses were styled with a round brush and a hairdryer, the temperature at the hairdryer's outlet being 80° C. The step of heating with a hairdryer was followed by two passes on each tress with smoothing iron at 210° C. For each tress, the time for passage of the smoothing iron was 15 s.

The tress width was measured at T0. Then all the tresses were placed in a humid enclosure, at 80% relative humidity, for 24 h. The width of these tresses was then measured to evaluate the volume uptake in a humid atmosphere (T 24 h).

The following results were obtained.

| | Control process: Steam heat | Invention process 1: Composition A + steam heat | Comparative process: Composition B + steam heat | Invention process 2: Composition A + heat |
|---|---|---|---|---|
| Width of the tress (cm) at T0 | 2 | 2 | 2 | 2 |
| Width of the tress at T = 24 hours | 13 | 5 | 15 | 5 |

Swelling observed in the tress is much less when the composition according to the invention is used in association with a heating tool (with or without steam) than when only a steam-heating tool is used, without a composition, or when the comparative composition is used. The composition according to the invention in association with a heating tool keeps good smoothing after 24 hours in a humid atmosphere.

Furthermore, there is less frizziness after treating the tresses with the composition according to the invention in association with a heating tool (with or without steam) than after treating with a steam-heating tool, without a composition, or after treating with the comparative composition.

The process according to the invention thus makes it possible to reduce the volume of the hair and does so durably in a humid environment.

What is more, the tresses of hair treated with the process according to the invention have good performance for visual smoothness and an even cosmetic feel that does not transfer.

The invention claimed is:

1. A method for reducing hair frizziness, comprising:
   a) applying to the hair a composition, the composition comprising an aqueous dispersion of divinyl dimethicone/dimethicone copolymer particles and polyurethane-34 particles;
   b) subsequently or simultaneously, heating the hair to a temperature ranging inclusively between 50° C. and 250° C. using at least one heating device; and
   c) applying steam to the hair using a device capable of generating steam, wherein steam is applied in an amount ranging between 0.5 g/min and 60 g/min, inclusively,
   wherein the composition reduces the frizziness of hair.

2. The method of claim 1, wherein the heating step is carried out at a temperature ranging inclusively between 90° C. and 250° C.

3. The method of claim 1, wherein the heating step b) follows the steam application step c.

4. The method of claim 1, wherein the heating step is performed using a heating device chosen from a straightening iron, curling iron, crimping iron, waving iron, hair drying hood, or hairdryer.

5. The method of claim 1, wherein the steaming step and the heating step are performed by a single device chosen from a steam-generating straightening iron, a steam-generating curling iron, a steam-generating crimping iron, or a steam-generating waving iron.

6. The method of claim 5, wherein the steaming step and the heating step are performed by a single device wherein the application of steam and the heating are dissociated.

7. The method of claim 1, wherein the divinyl dimethicone/dimethicone copolymer particles have an average size of less than or equal to about 2 microns.

8. The method of claim 1, wherein the divinyl dimethicone/dimethicone copolymer particles are present in an amount ranging from about 0.5% to about 15.0% by weight, relative to the total weight of the composition.

9. The method of claim 1, wherein the polyurethane-34 particles have an average diameter ranging up to about 1000 nm.

10. The method of claim 1, wherein the polyurethane-34 particles are present in an amount ranging from about 0.2% to about 10.0% by weight, relative to the total weight of the composition.

11. The method of claim 1, wherein the divinyl dimethicone/dimethicone copolymer particles and the polyurethane particles are present in a silicone/polyurethane weight ratio ranging from about 0.1 to about 10.

* * * * *